(12) United States Patent
Willms

(10) Patent No.: US 6,359,162 B1
(45) Date of Patent: Mar. 19, 2002

(54) METHOD FOR PRODUCING GLUFOSINATES AND INTERMEDIATE PRODUCTS FOR THE SAME

(75) Inventor: Lothar Willms, Hofheim (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/486,031

(22) PCT Filed: Aug. 8, 1998

(86) PCT No.: PCT/EP98/05053

§ 371 Date: Feb. 17, 2000

§ 102(e) Date: Feb. 17, 2000

(87) PCT Pub. No.: WO99/09039

PCT Pub. Date: Feb. 25, 1999

(30) Foreign Application Priority Data

Aug. 20, 1997 (DE) .......................... 197 36 125

(51) Int. Cl.$^7$ .............. C07F 9/30; C07F 9/32; C07F 9/6571
(52) U.S. Cl. ............... 558/82; 558/179; 558/346; 558/386; 562/11; 562/24
(58) Field of Search .................. 558/82, 179, 346, 558/386; 562/11, 24

(56) References Cited

U.S. PATENT DOCUMENTS

| 4,264,532 A | * | 4/1981 | Tsuruoka et al. |
|---|---|---|---|
| 4,521,348 A | | 6/1985 | Finke et al. |
| 4,692,541 A | | 9/1987 | Zeiss et al. |

FOREIGN PATENT DOCUMENTS

| DE | 35 08 573 A1 | 9/1986 |
|---|---|---|
| EP | 0 009 022 A1 | 3/1980 |
| EP | 0 011 245 A1 | 5/1980 |
| EP | 0 292 918 A1 | 11/1988 |

OTHER PUBLICATIONS

Mundy, Bradford P.; Ellerd, Michael G. "Name Reactions and Reagents in Organic Syntheses"; John Wiley and Sons: New York, 1988: p. 244.*

Ivan A. Natchev, J. Chem. Soc. Perkin. Trans. 1, pp. 125–131, 1989.

* cited by examiner

*Primary Examiner*—Fiona T. Powers
(74) *Attorney, Agent, or Firm*—Frommer Lawrence & Haug LLP

(57) ABSTRACT

Glufosinate and the 2-methyl analog thereof can be prepared in a multi-step synthesis from methylphosphorus compounds (II) with unsaturated keto compounds (III) via adducts (IV), subsequent reaction under the conditions of a Strecker synthesis and finally hydrolysis of the aminonitrile (V):

Step 1:

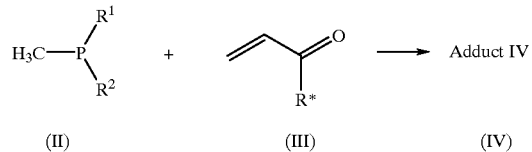

Step 2:

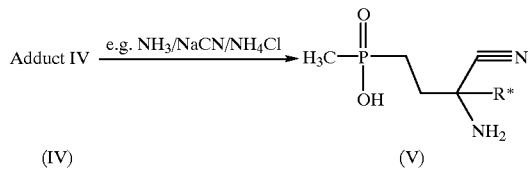

Step 3: Hydrolysis of (V) to give glufosinate

Depending on process conditions and substrates, various compounds can be identified as adducts (IV).

19 Claims, No Drawings

METHOD FOR PRODUCING GLUFOSINATES AND INTERMEDIATE PRODUCTS FOR THE SAME

The invention relates to the technical field of the processes for preparing biologically active compounds and precursors thereof, preferably of crop protection agents, in particular the herbicide glufosinate, also known as phosphinothricin.

Glufosinate (see formula (Ia)) is the common name for the active compound (D,L)-2-amino-4-[hydroxy(methyl)phosphinyl]butanoic acid, which is commercially available as monoammonium salt and is used as foliar herbicide (see DE-A-2717440, U.S. Pat. No. 4,168,963).

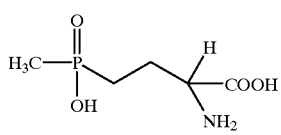

(Ia)

The herbicide can be employed for the non-selective control of weeds in fruit growing and viticulture, in plantation crops, in vegetable growing prior to sowing or transplanting, prior to direct sowing of maize or soya beans, and also on uncultivated land, such as roadsides, industrial terrain and railroad tracks (cf. Z. PflKrankh.PflSchutz, Special Edition IX, 431–440, 1981). Also known is the selective use for controlling weeds in crops of useful plants, such as, inter alia, maize and rapeseed, which have been made resistant by gene technology (cf. EP-A-0242246).

A large number of processes for preparing glufosinate have been disclosed. According to the variant described in EP-A-0011245 (U.S. Pat. No. 4,521,348), phosphorus-containing cyanohydrin derivatives of the formula

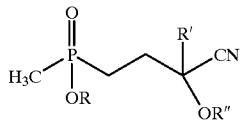

in which R is a hydrocarbon radical such as alkyl, haloalkyl, cycloalkyl, phenyl or benzyl, with or without substitution, R' is hydrogen, alkyl, phenyl or benzyl and R" is hydrogen, acyl, trialkylsilyl or alkylsulfonylalkyl, can be converted into aminonitriles, which in turn can be hydrolyzed to give glufosinate. According to EP-A-0011245, the preparation of the cyanohydrin derivatives is carried out by reaction of a monoalkyl methanephosphonate and an acroleincyanohydrin derivative of the formula

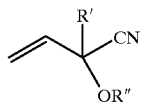

in which R' and R" are as defined above. The described process has the disadvantage that the phoshorus-containing derivative and its precursors have to be provided in the form of esters, whereas in the desired product glufosinate (Ia), the (hydroxy)(methyl)phosphinyl radical is present in hydrolyzed form.

It is an object of the present invention to provide an alternative process to the process described above, said process allowing the number of ester precursors to be reduced and being suitable for preparing glufosinate and related compounds.

The invention provides a process for preparing compounds of the formula (I),

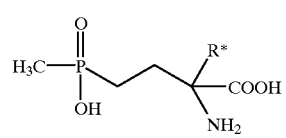

(I)

in which R* is hydrogen or $(C_1-C_4)$-alkyl, preferably H or methyl, or salts thereof with acids or bases, which comprises a) (Step 1)
reacting a trivalent methylphosphorus compound of the formula (II) with an unsaturated derivative of the formula (III), if appropriate in the presence of a condensing agent or activator and, if appropriate, alcohols, to give an adduct (IV), Step 1:

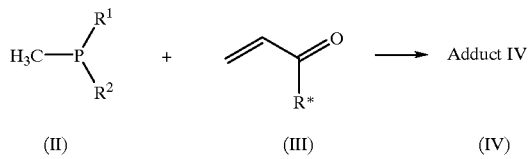

where in the formulae

R$^1$ and R$^2$ independently of one another are halogen, such as, for example, fluorine, chlorine, bromine or iodine, $(C_1-C_{18})$alkoxy with or without substitution, benzyloxy or phenoxy, which may also be substituted, or one of the radicals R$^1$ and R$^2$ is hydroxyl, and R* is as defined in formula (I), b) (Step 2)
the adduct (IV) is, if appropriate after hydrolytic ring opening to aldehydes (R*=H) or ketones (R*=alkyl) of the formula (IV') or salt thereof,

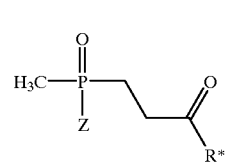

(IV')

in which Z is OH, R$^1$ or R$^2$, reacted under the conditions of a Strecker synthesis with ammonia/ammonium chloride and sodium cyanide or alternatively with mixtures of ammonia and hydrocyanic acid or with ammonia and a salt of hydrocyanic acid, such as, for example, ammonium cyanide or potassium cyanide, if appropriate in the presence of ammonium chloride, to give the α-aminonitriles of the formula (V) or a salt thereof, Step 2:

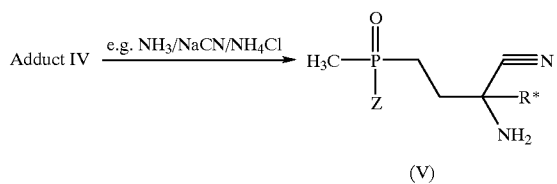

where in the formulae (IV') and (V) the radical R* is as defined in formula (I) and Z is as defined in formula (IV') or is OH, and c) (Step 3)

the compound of the formula (V) is hydrolyzed under acidic or basic conditions to give the compound of the formula (I) or the salt thereof.

In the abovementioned formulae and in the formulae used hereinbelow, the radicals alkyl, alkoxy, haloalkyl, haloalkoxy, alkylamino and alkylthio, and also the corresponding unsaturated radicals and/or radicals which are substituted in the carbon skeleton, may in each case be straight chain or branched. Unless specifically indicated, preference for these radicals is given to the lower carbon skeletons, for example those having 1 to 4 carbon atoms and, in the case of unsaturated groups, those having 2 to 4 carbon atoms. Alkyl radicals, also in the composed meanings such as alkoxy, haloalkyl, etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; cycloalkyl is a carbocyclic saturated ring system, for example having 3 to 8 ring atoms, for example cyclopropyl, cyclobutyl, cyclopentyl, cyclohexyl, etc.; alkenyl, alkynyl and cycloalkenyl radicals have the meaning of the possible unsaturated radicals which correspond to the alkyl or cycloalkyl radicals; alkenyl is, for example, allyl, 1-methylprop-2-en-1-yl, 2-methylprop-2-en-1-yl, but-2-en-1-yl, but-3-en-1-yl, methylbut-3-en-1-yl and 1-methylbut-2-en-1-yl; cycloalkenyl is, for example, cyclopentenyl or cyclohexenyl; alkynyl is, for example, propargyl, but-2-yn-1-yl, but-3-yn-1-yl or 1-methylbut-3-yn-1-yl. Alkenyl in the form "$(C_3-C_4)$ alkenyl" or "$(C_3-C_6)$-alkenyl" is preferably an alkenyl radical having 3 to 4 and 3 to 6 carbon atoms, respectively, where the double bond is not adjacent to the carbon atom which is attached to the rest of the molecule moiety of the compound (I) ("yl" position). This applies correspondingly to $(C_3-C_4)$-alkynyl, etc.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl_2$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and to other halogen-substituted radicals.

If substitutions are defined by "one or more radicals selected from a group of radicals", this includes both the substitution by one or more identical radicals and mono- or polysubstitution by different radicals.

Substituted radicals, such as substituted hydrocarbon radicals, for example substituted alkyl, alkenyl, alkynyl, aryl, phenyl., and benzyl, or substituted heterocyclyl, are, for example, a substituted radical derived from the unsubstituted parent radical, where the substituents are, for example, one or more, preferably 1, 2 or 3, radicals selected from the group consisting of halogen, alkoxy, haloalkoxy, alkylthio, hydroxyl, amino, nitro, cyano, azido, alkoxycarbonyl, alkylcarbonyl, formyl, carbamoyl, mono- and dialkyl-aminocarbonyl, substituted amino such as acylamino, mono- or dialkyl-amino, and alkylsulfinyl, haloalkylsulfinyl, alkylsulfonyl, haloalkylsulfonyl and, in the case of cyclic radicals, also alkyl and haloalkyl, and unsaturated aliphatic radicals corresponding to the abovementioned saturated hydrocarbon-containing radicals, such as alkenyl, alkynyl, alkenyloxy, alkynyloxy etc. Preferred radicals having carbon atoms are those having 1 to 4 carbon atoms, in particular 1 or 2 carbon atoms. Preferred substituents are usually those from the group consisting of halogen, for example fluorine and chlorine, $(C_1-C_4)$alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given to the substituents methyl, methoxy and chlorine.

Phenyl with or without substitution is preferably phenyl which is unsubstituted or mono- or polysubstituted, preferably up to trisubstituted, by identical or different radicals selected from the group consisting of halogen, $(C_1-C_4)$-alkyl, $(C_1-C_4)$-alkoxy, $(C_1-C_4)$-haloalkyl, $(C_1-C_4)$haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is the radical of an organic acid, for example the radical of a carboxylic acid, and radicals of acids derived therefrom, such as the thiocarboxylic acid, iminocarboxylic acids with or without N-substitution, or the radical of carbonic acid monoesters, carbaminic acids with or without N-substitution, sulfonic acids, sulfinic acids, phosphonic acids, phosphinic acids. Acyl is, for example, formyl, alkylcarbonyl such as $(C_1-C_4$-alkyl)-carbonyl, phenylcarbonyl, where the phenyl ring may be substituted, for example as shown above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

Compounds of the formula (II) are known or can be prepared by known processes, see, for example, J. B. Miles et al. in Org. Prep. Proc. Int., 11 (1), 11 (1979); B. M. Gladshtein et al., Zh. Obshch. Khim. 39, 1951 (1969); DAS 1098940 (1959), Farbf. Bayer, Boetzel et al., J. Fluorine Chem. 68, 11 (1994); Hoffmann et al., JACS 80, 1150 (1958).

In the compounds of the formula (II), $R^1$ and $R^2$ independently of one another are preferably halogen, such as, for example, fluorine, chlorine, bromine or iodine, $(C_1-C_6)$ alkoxy, $(C_1-C_6)$haloalkoxy, benzyloxy or phenoxy, where each of the two last-mentioned radicals is unsubstituted or substituted by one or more radicals selected from the group consisting of halogen, alkyl, haloalkyl, alkylthio, nitro, cyano, alkylsulfonyl and haloalkylsulfonyl, preferably in each case having 1 to 6 carbon atoms, in particular 1 to 4 carbon atoms, in the alkyl moiety, or one of the radicals $R^1$ and $R^2$ is preferably hydroxyl.

Particularly preferably, $R^1$ and $R^2$ are each $(C_1-C_4)$ alkoxy.

The compounds of the formula (III) are basic chemicals and therefore also known.

The adducts (IV) may have various structures. Intermediates which are possible in some cases are 2-methyl-1,2- oxa-4-phospholenes of the formula (IV*), i.e. the subsequent reactions are consistent with an intermediate of the formula (IV*):

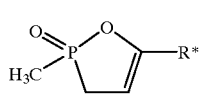
(IV*)

In certain cases, the compounds of the formula (IV*) occur as intermediates which cannot be detected, or do not occur as intermediates at all, depending on which activators or condensing agents or reactive additives such as alcohols are employed in the addition/condensation reaction.

In a preferred embodiment, preference is given to reacting compounds of the formula (II-1) with a compound of the formula (III) in the presence of anhydrides $A_2O$, preferably carboxylic anhydrides, and alcohols ROH, to give adducts (IV-1), the latter being semiacetals or a salt thereof,

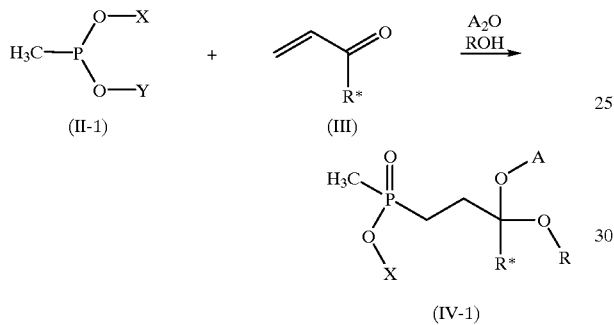

in which
—O—X and —O—Y correspond to the radicals $R^1$ and $R^2$, respectively, if these are radicals of alcohols, i.e. each of the radicals X and Y independently of one another is H or $(C_1-C_{15})$-alkyl which is unsubstituted or substituted, benzyl or phenyl, where each of the two abovementioned radicals is unsubstituted or substituted, preferably unsubstituted or substituted by one or more radicals selected from the group consisting of halogen, alkyl, haloalkyl, alkylthio, nitro, cyano, alkylsulfonyl and haloalkylsulfonyl, preferably in each case having 1 to 6 carbon atoms, in particular 1 to 4 carbon atoms in the alkyl moiety, and X and Y are preferably identical radicals, and in particular X, Y and R are identical radicals, R* is as defined in formula (I), preferably H, A is an acyl radical, preferably the acyl radical of a carboxylic acid having 1 to 6 carbon atoms, in particular 1 to 4 carbon atoms, R is a radical selected from the group of the radicals defined for X and Y, preferably the same radical as X or Y.

Particularly preferably

X, Y and R are in each case identical radicals selected from the group consisting of $(C_1-C_6)$alkyl, phenyl or benzyl, in particular $(C_1-C_4)$alkyl, for example methyl, ethyl, n-, i-propyl, n-, i-, s- or t-butyl.

Correspondingly, the compounds (IV') and (V) are, in the preferred variant (starting from compounds (II-1)), compounds of the formula (IV'-1) and (V-1) or salts thereof, respectively,

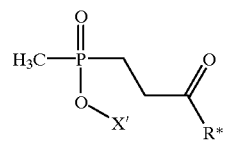
(IV'-1)

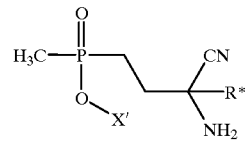
(V-1)

in which X'=H or X and R* and X are as defined above, or salts thereof.

2-Methyl-1,2-oxa-4-phospholenes of the formula (IV*) and the semiacetals of the formula (IV-1) have hitherto been unknown, as have been the aminonitriles of the formula (V-2) (=formula (V) where Z=OH)

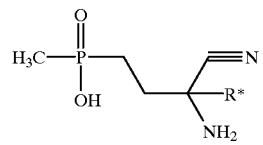
(V-2)

and they therefore also form part of the subject matter of the present invention.

From the 1,2-oxa-4-phospholenes (IV*), only some higher homologs are known. Thus, phenyldichlorophosphane (IIa) reacts with α,β-unsaturated ketones (VI) with addition of acetic anhydride to give the 2-phenyl-2-oxo-1,2-oxa-4-phospholenes (VII) (K. Bergesen, Acta Chem. Scand. 19, 1784 (1965)),

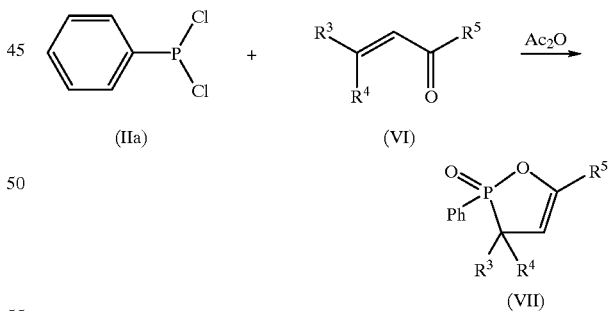

in which $R^3$ and $R^4$ are hydrogen, methyl or phenyl and $R^5$ is methyl or phenyl.

Furthermore, it is known that ethyldichlorophosphane IIb reacts with methyl vinyl ketone (VIa) to give 5-methyl-2-ethyl-2-oxo-1,2-oxa-4-phospholene (VIIa) (A. N. Pudovik et al., Isv. Akad. Nauk. SSSR, Ser. Khim. (Engl. version) 2543 (1970));

Et ethyl in formula IIb; Me=methyl in formula VIIa; Ac=acetyl;

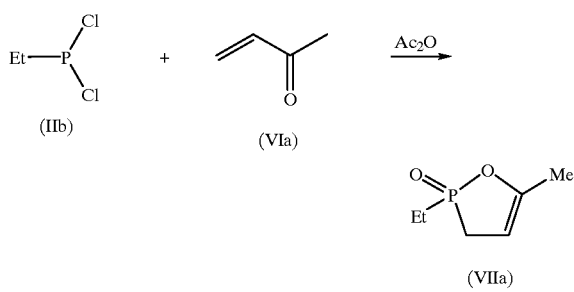

Finally, the reaction of 2-thienyldichlorophosphane (IIc) with α,β-unsaturated ketones gives 2-thienyl-2-oxo-1,2-oxa-4-phospholenes (VIIb) (R. Z. Aliev, Isv. Akad. Nauk., SSSR, Ser. Khim (Engl. version), 2719 (1973)),

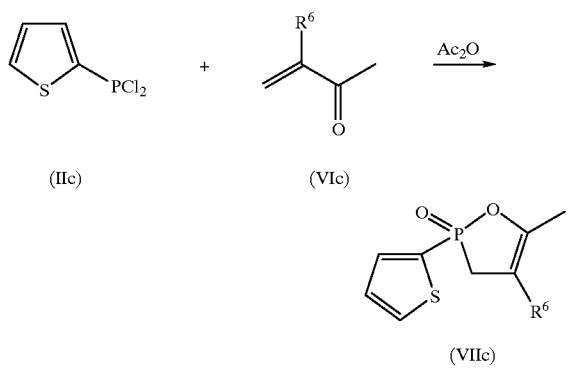

in which $R^6$ is hydrogen or methyl.

Analogous reactions, for example with methyldichlorophosphane which is highly reactive compared to phenyldichlorophosphane (cf. H. Heydt et al., Methoden der Organischen Chemie XII E2, p. 29 (1982)) and methanephosphonous acid diesters have hitherto not been described in the literature. Analogous reactions with acrolein (III; $R^2$=H) are likewise not known.

Because the components (II) and (III) are much more reactive, and because of the complex reaction mixture or the complex course of the reaction in step 1, it is extremely surprising that the process according to the invention can be realized in high yields via the intermediates (adducts IV) to give the α-aminonitrile derivatives (V) or (V-1) and subsequently the compounds (I).

In step 1, the process according to the invention is generally carried out by reacting compounds of the formula (II) or (II-1) with unsaturated compounds of the formula (III), preferably in the presence of a condensing agent or activator. Suitable activators/condensing agents are substances which are suitable for promoting or catalyzing the addition of the phosphorus component to the α,β-unsaturated keto compound (III). Suitable condensing agents or activators are carboxylic anhydrides, preferably anhydrides of alkanecarboxylic acids having 1 to 6 carbon atoms, for example acetic anhydride or propionic anhydride.

Also suitable are mixtures of the anhydrides with certain proportions of alcohols ROH, where R is as defined above.

The reaction of compounds (II) and (III) can be carried out without solvent or in the presence of an organic solvent, for example in the presence of aliphatic or aromatic hydrocarbons which may be halogenated, such as dichloromethane, toluene, xylene, chlorobenzene, or ethers, such as dioxane, or alcohols, such as ethanol, n-butanol, etc., or mixtures of these exemplary solvents.

The phosphorus components of the formula (II) are employed in molar ratios which can deviate considerably from the stoichiometry, preferably in molar ratios of 1:2 to 2:1, but in particular essentially in equimolar amounts, based on the component (III).

If the reaction of the components (II) and (III) is carried out in the presence of an anhydride $A_2O$, such as, for example, acetic anhydride or propionic anhydride, suitable anhydride inputs are usually in the range of from more than 0 to 400 mol %, preferably amounts of from 50 to 150 mol %, based on the starting component (II) or (III), which is employed in the lowest molar amount.

If the reaction of the components (II-1) and (III) is carried out in the presence of the anhydride $A_2O$, for example acetic anhydride, and an alcohol ROH, for example ($C_1$–$C_5$) alkanol such as ethanol, preference is given to using 50 to 150 mol % of acetic anhydride and 50 to 200 mol % of alcohol, in particular in the anhydride:alcohol ratio of 1:1 to 1:1.5, based on the starting component (II) or (III), which is employed in the lowest molar amount.

The reaction, according to the invention, of compounds (II) and (III) succeeds generally at reaction temperatures between –80° C. and +200° C., preferably between –10° C. and +60° C. The duration of the reaction depends in general on the reaction temperature, the size of the batch, the specific reactants, the solvent and the condensing agents/activators and is, for example, in the range of 0.5–48 hours (h), preferably 0.5–18 h.

Surprisingly, the reaction, according to the invention, of the intermediates (IV) and (IV-1) to give the desired α-aminonitriles (V) and (V-1), respectively, (step 2) can be carried out under conditions which are known analogously to the preparation of aminonitriles from aldehydes or ketones by the type of the "Strecker synthesis" (see textbooks and handbooks of organic chemical synthesis). According to one possible procedure, the reaction solution which contains the crude product (IV) or (IV-1) is added to a solution or suspension comprising an alkali metal cyanide and ammonium chloride in aqueous ammonia solution. It is also possible to employ mixtures of the abovementioned organic solvents, such as, for example, toluene, xylene, chlorobenzene, dichloromethane, ethanol, butanol etc., for this purpose. Instead of alkali metal cyanides, it is also possible to use alkaline earth metal cyanides or ammonium cyanide, or solutions of hydrocyanic acid in ammonia.

The cyanides or the hydrocyanic acid are employed, for example, in amounts of 80–130 mol %, but preferably in essentially equimolar amounts, based on the components of the formula (IV). The amount of ammonia based on the compound (IV) is, for example, between 100 and 800 mol %, preferably from 100 to 400 mol %. The reactions of the compounds (IV) under the conditions of the Strecker synthesis are carried out, for example, at from –10° C. to 100° C., preferably at 0–45° C.

The compounds of the formula (V) or (V-1) are preferably obtained as salts in which the acidic hydrogen atom at the phosphinoyl group is replaced by a cation equivalent, preferably by a cation equivalent such as, for example, $Li^+$, $Na^+$, $K^+$, $(Mg^{2+})_{1/2}$, $(Ca^{2+})_{1/2}$, $NH_4^+$.

Alternatively, it is possible to initially purify the intermediates (IV) or (IV-1) by distillation or extractive methods and to react them in purified form to give the aminonitriles (V) or (V-1).

In a further variant, the intermediates (adducts IV) or (IV-1) are initially hydrolyzed with water to give the aldehydes or ketones of the formula (IV') or (IV-1) and reacted in a further step to give the α-aminonitriles (V) or (V-1).

In the formula (IV'), R* is hydrogen or $(C_1-C_4)$-alkyl. The compound where R*=hydrogen and Z=hydroxyl or salts thereof are novel compounds in the methylphosphinic acid series and therefore also form part of the subject matter of the invention, i.e. the compound of the formula (IV'-2) or salts thereof

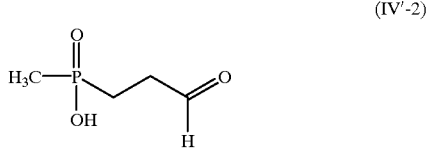

(IV'-2)

However, the compound (IV) where R*=methyl and Z=hydroxyl is known (L. D. Quin et al., J. Org. Chem. 39, 686 (1974)).

According to step 3 of the process according to the invention, the α-aminonitriles of the formula (V) or (V-1) are useful intermediates which, in analogy with the process conditions known from the literature (Houben-Weyl, Methoden der Organischen Chemie XI/2, p. 305 and p. 371, 1958), can be hydrolyzed both in acidic and in basic medium, to give the biologically active amino acids of the formula (I), in particular glufosinate of the formula (Ia).

Compared with known processes for the synthesis of the herbicidal amino acid (Ia), the process according to the invention has a number of advantages, for example, the additional esterification of the phosphorus components of the intermediates (IV), (IV') and (V) of the intermediates is unnecessary. Moreover, the process can optionally be carried out separately for each step, or as a one-pot process over all 3 steps.

Thus, the essential PC linkage for building up the amino acid side chain can be carried out in one step, for example with methyldihalophosphanes or, preferably, methanephosphonous acid diesters (II) or (II-1) and olefins (III), without the complicated conversion of, for example, methyldichlorophosphane to methanephosphonous acid monoesters being necessary. Moreover, in contrast to the process known from EP-A-0011245, the radical addition of the methanephosphonous acid monoesters to acrolein derivatives, which readily leads to by-products, is avoided. In the process according to the invention it is possible to employ, for example, the readily obtainable olefin components acrolein or methyl vinyl ketone directly, without derivatization being necessary. Furthermore, the α-aminonitriles (V) or (V-1) are obtained in the process according to the invention with a free phosphinic acid or phosphinate grouping, so that in the last step of the synthesis only the nitrile group has to be hydrolyzed to give the free amino acid. Deblocking of the phosphinic ester group to the free phosphinic acid, which is required in the prior art method mentioned above, is thus superfluous.

The examples below illustrate the process, without limiting the possible process conditions. Unless specifically defined otherwise, the amounts stated are based on weight.

EXAMPLE 1

2-Amino-2-methyl-4-(hydroxymethylphosphinyl) butyric acid, ammonium salt

At room temperature and under an atmosphere of inert gas, 7.01 g (0.10 mol) of methyl vinyl ketone are admixed with 10.21 g (0.10 mol) of acetic anhydride. With cooling at at most 25–30° C., 13.61 g (0.10 mol) of diethyl methanephosphonate are subsequently added dropwise. The reaction mixture is stirred at 30° C. for approximately 6 hours. At 20–25° C., the mixture is then added dropwise to a solution of 4.41 g (0.09 mol) of sodium cyanide and 9.63 g (0.18 mol) of ammonium chloride in 50 ml of ammonia solution (25% strength). The mixture is stirred at 25° C. for another 4 hours and the crude aminonitrile is then rapidly added dropwise without isolation to 200 ml of hydrochloric acid (37% strength). The reaction mixture is subsequently boiled under reflux for approximately 4 hours, while ethanol and acetic acid are distilled off. The mixture is concentrated using a rotary evaporator, a pH of approximately 9 is set using ammonia solution and the desired product is freed of salts by recrystallization from methanol.

This gives 19.1 g (corresponding to 94.5% of theory) of 2-amino-2-methyl-4-(hydroxymethylphosphinyl)butyric acid, ammonium salt.

$^1$H NMR (D$_2$O): 1.56 (d, J=14 Hz, 3H); 1.63 (s, 3H); 1.7–2.3 (m, 4H) $^{31}$P NMR (D$_2$O): 54.4.

EXAMPLE 2

2-Amino-2-methyl-4-(hydroxymethylphosphinyl) butyric acid, ammonium salt

At room temperature, 2.10 g (0.03 mol) of methyl vinyl ketone and 3.06 9 (0.03 mol) of acetic anhydride are dissolved in 20 ml of dichloromethane. At 25–28° C., 3.51 g (0.03 mol) of methyldichlorophosphane are subsequently rapidly added dropwise and the mixture is stirred at approximately 30° C. for 3 hours and then added dropwise to a solution of 1.375 g (0.0275 mol) of sodium cyanide and 2.94 g (0.055 mol) of ammonium chloride in 25 ml of ammonia (25% strength). The mixture is stirred at 28–30° C. for approximately 4 hours and the two-phase crude aminonitrile solution is added dropwise at 25–30° C. to 100 ml of hydrochloric acid (37% strength). The mixture is subsequently heated under reflux for approximately 4 hours and worked-up as under Example 1.

This gives 5.83 g (corresponding to 92% of theory) of 2-amino-2-methyl-4-(hydroxymethylphosphinyl)butyric acid, ammonium salt.

$^1$H NMR (D$_2$O): 1.57 (d, J=14 Hz, 3H); 1.65 (s, 3H); 1.7–2.3 (m, 14H). $^{31}$P NMR: 54.5

EXAMPLE 3

2-Amino-4-(hydroxymethylphosphinyl)butyric acid, ammonium salt

At room temperature, 5.61 g (0.10 mol) of freshly distilled acrolein are added to 10.21 g (0.10 mol) of acetic anhydride. At 25–30° C., 13.61 g (0.10 mol) of diethyl methanephosphonate are subsequently added dropwise. The mixture is stirred at 30° C. for 2 hours and then, at 25–28° C., added dropwise to a solution of 4.9 g (0.10 mol) of sodium cyanide and 10.7 g (0.20 mol) of ammonium chloride in 50 ml of ammonia (25% strength). After 2 hours at 30° C., the crude aminonitrile is added dropwise to 200 ml of hydrochloric acid (37% strength). The mixture is subsequently heated under reflux for 2 hours, while ethanol and acetic acid are distilled off. The mixture is concentrated using a rotary evaporator, a pH of approximately 9 is set using ammonia solution and the product is purified by crystallization from methanol. This gives 19.4 g (98% of theory) of 2-amino-4-(hydroxymethylphosphinyl)butyric acid, ammonium salt.

$^1$H NMR (D$_2$O): 1.60 (d,14 Hz, 3H); 1.8–2.4 (m, 4H); 4.28 (t, J=6 Hz, 1H). $^{31}$P NMR (D$_2$O): 55.9.

EXAMPLE 4

2-Amino-2-methyl-4-(hydroxymethylphosphinyl) butyric acid, ammonium salt

At room temperature and under an atmosphere of inert gas, 14.02 g (0.20 mol) of methyl vinyl ketone are admixed with 20.42 g (0.20 mol) of acetic anhydride. With cooling and at at most 25 to 30° C., a mixture of 27.22 g (0.20 mol) of diethyl methanephosphonate and 9.2 g (0.2 mol) of ethanol is subsequently added dropwise. The reaction mixture is stirred at 30° C. for approximately 6 hours. At 20 to 25° C., the mixture is then added dropwise to a solution of 8.82 g (0.18 mol) of sodium cyanide and 19.26 g (0.36 mol) of ammonium chloride in 100 ml of ammonia solution (25% strength). The mixture is stirred at 25° C. for another 4 hours and the crude aminonitrile is then rapidly added dropwise without isolation to 400 ml of hydrochloric acid (37% strength). The reaction mixture is subsequently boiled under reflux for approximately 4 hours, while ethanol and acetic acid are distilled off. The mixture is concentrated using a rotary evaporator, a pH of approximately 9 is set using ammonia solution and the desired product is freed of salts by recrystallization from methanol.

This gives 38.8 g (corresponding to 96% of theory) of 2-amino-2-methyl-4-(hydroxymethylphosphinyl)butyric acid, ammonium salt (physical data see Ex. 1).

EXAMPLE 5

2-Amino-4-(hydroxymethylphosphinyl)butyric acid, ammonium salt

At room temperature, 5.61 g (0.10 mol) of freshly distilled acrolein are added to 10.21 g (0.10 mol) of acetic anhydride. At 25 to 30° C., this mixture is subsequently added dropwise to 13.61 g (0.10 mol) of diethyl methanephosphonate and 4.6 g (0.1 mol) of ethanol. The mixture is stirred at 30° C. for 2 hours and then, at 25 to 28° C., added dropwise to a solution of 4.9 g (0.10 mol) of sodium cyanide and 10.7 g (0.20 mol) of ammonium chloride in 50 ml of ammonia (25% strength). After 2 hours at 30° C., the crude aminonitrile is added dropwise to 200 ml of hydrochloric acid (37% strength). The mixture is subsequently heated under reflux for 2 hours, while ethanol and acetic acid are distilled off. The mixture is concentrated using a rotary evaporator, a pH of approximately 9 is set using ammonia solution and the product is purified by crystallization from methanol. This gives 19.6 g (99% of theory) of 2-amino-4-(hydroxymethylphosphinyl)-butyric acid, ammonium salt.

$^1$H NMR (D$_2$O): 1.60 (d, 14 Hz, 3H); 1,8–2.4 (m, 4H); 4.28 (t, J=6 Hz, 1 H). $^{31}$P NMR (D$_2$O): 55.9.

EXAMPLE 6

2-Amino-4-(hydroxymethylphosphinyl)butyric acid, ammonium salt

At room temperature, 5.61 g (0.10 mol) of freshly distilled acrolein are added to 10.21 g (0.10 mol) of acetic anhydride. At 25 to 30° C., this mixture is subsequently added dropwise to 16.41 g (0.10 mol) of dibutyl methanephosphonate and 14.8 g (0.2 mol) of n-butanol. The mixture is stirred at 30° C. for 2 hours and then, at 25 to 28° C., added dropwise to a solution of 4.9 g (0.10 mol) of sodium cyanide and 10.7 g (0.20 mol) of ammonium chloride in 50 ml of ammonia (25% strength). After 2 hours at 30° C., the crude aminonitrile is added dropwise to 200 ml of hydrochloric acid (37% strength). The mixture is subsequently heated under reflux for 2 hours, while ethanol and acetic acid are distilled off. The mixture is concentrated using a rotary evaporator, a pH of approximately 9 is set using ammonia solution and the product is purified by crystallization from methanol. This gives 17.8 g (90% of theory) of 2-amino-4-(hydroxymethylphosphinyl)-butyric acid, ammonium salt.

$^1$H NMR (D$_2$O): 1.60 (d, 14 Hz, 3H); 1.8–2.4 (m, 4H); 4.28 (t, J 6 Hz, 1H). $^{31}$P NMR (D$_2$O): 55.9.

What is claimed is:

1. A process for preparing compounds of the formula I

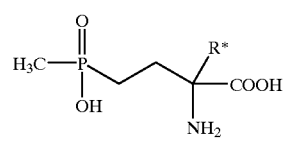

(I)

in which R* is hydrogen or (C$_1$–C$_4$)-alkyl, or salts thereof with acids or bases, which comprises a) (Step 1)

reacting a trivalent methylphosphorus compound of the formula (II) with an unsaturated derivative of the formula (III), in the presence of a condensing agent or activator selected from substances which promote or catalyze the addition of the phosphorous component to the α, β-unsaturated keto compound and, if appropriate, alcohols, to give an adduct (IV), Step 1:

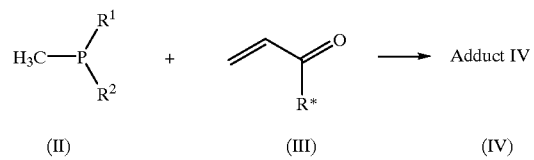

where in the formulae

R$^1$ and R$^2$ independently of one another are (C$_1$–C$_{18}$) alkoxy with or without substitution, benzyloxy or phenoxy, which may also be substituted, or one of the radicals R$^1$ and R$^2$ is hydroxyl, and R* is as defined in formula (I), b) (Step 2)

the adduct (IV) is, if appropriate after hydrolysis to aldehydes (R*=H) or ketones (R*=alkyl) of the formula (IV'), or to a salt thereof

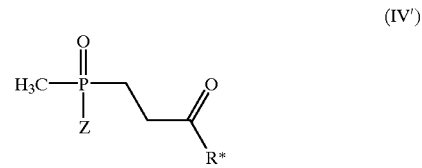

(IV')

in which Z is OH, R$^1$ or R$^2$, reacted under the conditions of a Strecker synthesis with ammonia/ammonium chloride and sodium cyanide or alternatively with mixtures of ammonia and hydrocyanic acid or with ammonia and a salt of hydrocyanic acid, if appropriate in the presence of ammonium chloride, to give the α-aminonitriles of the formula (V) or a salt thereof, Step 2:

Adduct IV ⟶ 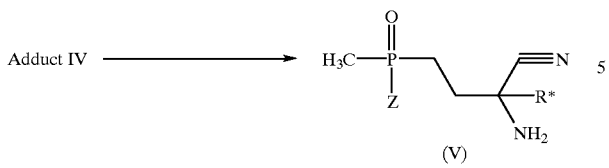

(V)

where in the formulae (IV') and (V) the radical R* is as defined in formula (I) and Z is as defined in formula (IV') or is OH, and c) (Step 3)

the compound of the formula (V) is hydrolyzed under acidic or basic conditions to give the compound of the formula (I) or salts thereof.

2. The process as claimed in claim 1, wherein $R^1$ and $R^2$ independently of one another are $(C_1-C_6)$alkoxy, $(C_1-C_6)$ haloalkoxy, benzyloxy or phenoxy, where each of the two last-mentioned radicals is unsubstituted or substituted by one or more radicals selected from the group consisting of halogen, alkyl, haloalkyl, alkylthio, nitro, cyano, alkylsulfonyl and haloalkylsulfonyl having in each case 1 to 6 carbon atoms in the alkyl moiety, or one of the radicals $R^1$ or $R^2$ is hydroxyl.

3. The process as claimed in claim 1, wherein in step 1, as compounds (II), compounds of the formula (II-1) are reacted with a compound of the formula (III) in the presence of anhydrides $A_2O$ and alcohols ROH to give adducts (IV) of the formula (IV-1),

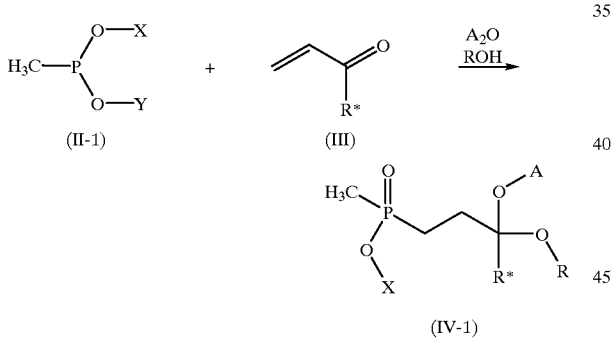

in which each of the radicals X and Y independently of one another is H or $(C_1-C_8)$alkyl which is unsubstituted or substituted, benzyl or phenyl, where each of the two abovementioned radicals is unsubstituted or substituted, and A is an acyl radical, R is $(C_1-C_{18})$alkyl, which is unsubstituted or substituted, benzyl or phenyl, where each of the two radicals above is unsubstituted or substituted.

4. The process as claimed in claim 3, wherein

X, Y and R are each $(C_1-C_4)$ alkyl,

A is an acyl radical of an alkanecarboxylic acid having 1 to 6 carbon atoms and

R* is a hydrogen atom.

5. A process for preparing compounds of the formula (I),

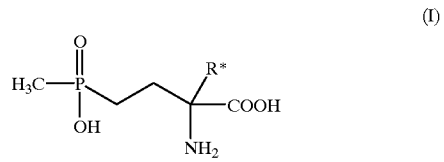

(I)

in which

R* is hydrogen or $(C_1-C_4)$alkyl, or salts thereof with acids or bases, which comprises hydrolyzing a compound of the formula (V-2) or salts thereof,

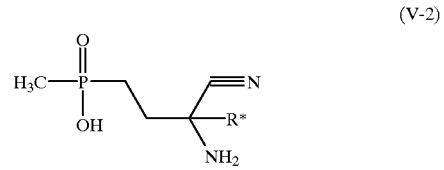

(V-2)

in which

R* is as defined in formula (I) under acidic or basic conditions to give the compound of the formula (I) or salts thereof.

6. The process as claimed in claim 5, wherein the compound of the formula (V-2) or a salt thereof is prepared from compounds of the formula (IV*),

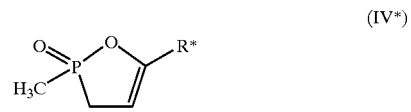

(IV*)

in which

R* is as defined in formula (V-2), if appropriate after hydrolytic ring opening to aldehydes or ketones of the formula (IV'),

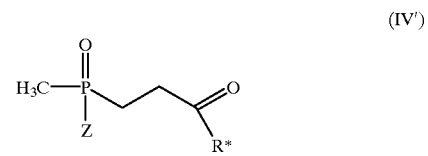

(IV')

in which

Z=OH and R* is as defined in formula (V-2), by reaction under the conditions of a Strecker synthesis with ammonia/ammonium chloride and sodium cyanide or alternatively with mixtures of ammonia and hydrocyanic acid or with ammonia and a salt of hydrocyanic acid, if appropriate in the presence of ammonium chloride, to give the α-aminonitriles of the formula (V-2) or a salt thereof.

7. A process of preparing compounds of the formula (V) or a salt thereof (V)

$$H_3C-\underset{Z}{\underset{\|}{\overset{O}{P}}}-CH_2-CH(R^*)(NH_2)-C\equiv N$$

in which

Z is OH or OX, wherein

X is H or $(C_1-C_{18})$alkyl with or without substitution, benzyl or phenyl, with or without substitution, and R* is H or $(C_1-C_4)$alkyl, comprising reacting compounds of the formula (IV-1), (IV-1)

$$H_3C-\underset{OX}{\underset{\|}{\overset{O}{P}}}-CH_2-C(R^*)(OA)(OR)$$

in which

X is $(C_1-C_{18})$alkyl, with or without substitution, benzyl or phenyl, with or without substitution, if Z=OH in formula (V), or is as defined in OX in formula (V), if Z=OX in formula (V), A is an acyl radical, R is $(C_1-C_{18})$alkyl, with or without substitution, benzyl or phenyl, with or without substitution, and R* is as defined in formula (V), if appropriate after hydrolysis to aldehydes or ketones of the formula (IV'), (IV')

$$H_3C-\underset{Z}{\underset{\|}{\overset{O}{P}}}-CH_2-C(=O)R^*$$

wherein Z is OH or, if Z is OX in formula (V), is OX as defined in formula (IV) and formula (V), and R* is defined as in formula (V), under the conditions of Strecker synthesis with ammonia/ammonium chloride and sodium cyanide or alternatively with mixtures of ammonia and hydrocyanic acid or with ammonia and a salt of hydrocyanic acid, if appropriate in the presence of ammonium chloride, to give the α-aminonitriles of the formula (V) or a salt thereof.

8. A compound of the formula (V-2) or a salt thereof with acids and bases, (V-2)

$$H_3C-\underset{OH}{\underset{\|}{\overset{O}{P}}}-CH_2-CH(R^*)(NH_2)-C\equiv N$$

in which

R* is H or $(C_1-C_4)$alkyl.

9. A compound of the formula (IV*), (IV*)

in which

R* is hydrogen or $(C_1-C_4)$ alkyl.

10. The process for preparing compounds of the formula (IV*) as claimed in claim 9 wherein a trivalent methylphosphorus compound of the formula (II) is reacted with an unsaturated derivative of the formula (III) in the presence of a condensing agent or activator to give a 1,2-oxa-4-phospholene of the formula (IV*), $$H_3C-P(R^1)(R^2) \quad + \quad CH_2=CH-C(=O)R^* \quad \longrightarrow$$

(II)      (III)

(IV*)

where in the formulae (II) and (III)

$R^1$ and $R^2$ independently of one another are $(C_1-C_{18})$ alkoxy, with or without substitution, benzyloxy or phenyloxy, with or without substitution, or one of the radicals $R^1$ and $R^2$ is hydroxyl, and R* is as defined in formula (IV*).

11. A compound of the formula (IV-1), (IV-1)

$$H_3C-\underset{OX}{\underset{\|}{\overset{O}{P}}}-CH_2-C(R^*)(OA)(OR)$$

in which

X is H or $(C_1-C_{18})$alkyl, with or without substitution, benzyl or phenyl, with or without substitution, A is an acyl radical, R is $(C_1-C_{18})$alkyl, with or without substitution, benzyl or phenyl, with or without substitution, and R* is H or $(C_1-C_4)$alkyl, or a salt thereof.

12. The process for preparing compounds of the formula (IV-1) or salts thereof as claimed in claim 11, wherein compounds of the formula (II-1) are reacted with a compound of the formula (III) in the presence of anhydrides $A_2O$ and alcohols ROH to give the adducts of the formula (IV-1) or salts thereof,

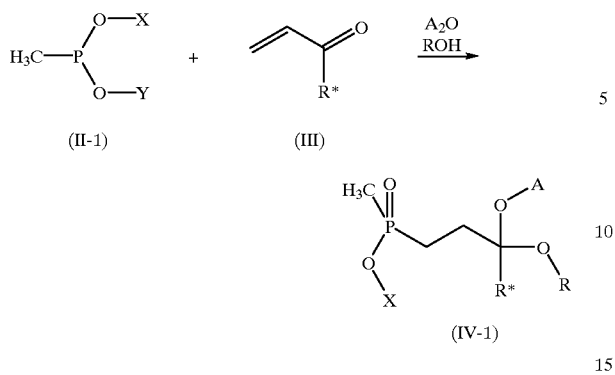

(II-1)  (III)  (IV-1)

in which
each of the radicals X and Y independently of one another is H or ($C_1$–$C_{18}$) alkyl which is unsubstituted or substituted, benzyl or phenyl, where each of the two abovementioned radicals is unsubstituted or substituted, and
A is an acyl radical,
R is ($C_1$–$C_{18}$) alkyl, which is unsubstituted or substituted, benzyl or phenyl, where each of the two radicals above is unsubstituted or substituted.

13. The process as claimed in claim 12, wherein from 50 to 150 mol % of anhydride $A_2O$ and from 50 to 200 mol % of alcohol ROH, based on the starting component (II-1) or (III) which has the lowest molarity, are employed.

14. A process for preparing compounds of the formula (I),

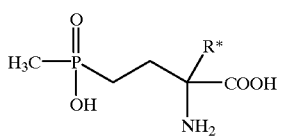

(I)

in which
R* is hydrogen or ($C_1$–$C_4$)alkyl, or salts thereof with acids or bases, which comprises reacting compounds of the formula (IV-I),

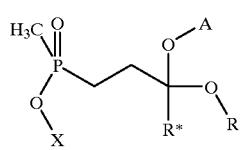

(IV-1)

in which
R* is as defined in formula (I), each of the radicals X and Y independently of one another is H or ($C_1$–$C_{18}$)alkyl which is unsubstituted or substituted, benzyl or phenyl, where each of the two abovementioned radicals is unsubstituted or substituted, and
A is an acyl radical, and
R is ($C_1$–$C_{18}$)alkyl, which is unsubstituted or substituted, benzyl or phenyl, where each of the two radicals above is unsubstituted or substituted, if appropriate after hydrolysis to aldehydes (R*=H) or ketones (R*=alkyl) of the formula (IV'),

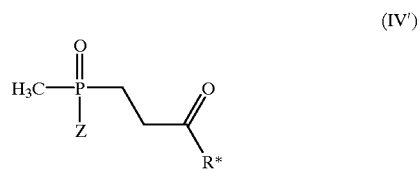

(IV')

in which
Z is OH or OX, or to salts thereof under the conditions of a Strecker synthesis with ammonia/ammonium chloride and sodium cyanide or alternatively with mixtures of ammonia and hydrocyanic acid or with ammonia and a salt of hydrocyanic acid, if appropriate in the presence of ammonium chloride, to give the α-aminonitriles of the formula (V) or a salt thereof:

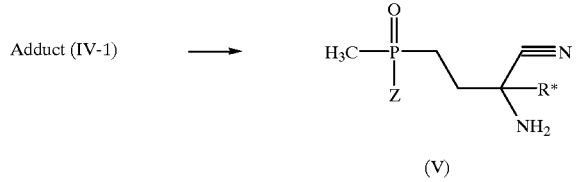

(V)

where in the formulae (IV') and (V) the radical R* is as defined in formula (I), X is as defined in formula (IV-1) and Z in formula (V) is as defined in formula (IV') or is OH, and
the compound of the formula (V) or a salt thereof is hydrolyzed under acidic or basic conditions to give the compound of the formula (I) or a slat thereof.

15. The process according to claim 1, wherein the condensing agent or activator is a carboxylic acid anhydride.

16. A process for preparing compounds of the formula I

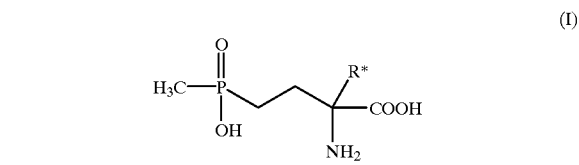

(I)

in which
R* is hydrogen or ($C_1$–$C_4$)-alkyl, or salts thereof with acids or bases, which comprises
a) (Step 1)
reacting a trivalent methylphosphorus compound of the formula (II) with an unsaturated derivative of the formula (III), in the presence of a condensing agent or activator, wherein the condensing agent or activator is a carboxylic acid anhydride, and, if appropriate, alcohols, to give an adduct (IV), Step 1:

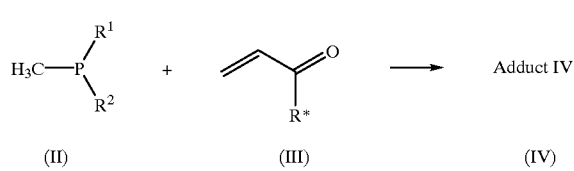

(II)  (III)  (IV)

where in the formulae $R^1$ and $R^2$ independently of one another are ($C_1$–$C_{18}$) alkoxy with or without substitution, benzyloxy or phenoxy, which may also be substituted, or one of the radicals $R^1$ and $R^2$ is hydroxyl, and R* is as defined in formula (1), b) (Step 2)

the adduct (IV) is, if appropriate after hydrolysis to aldehydes (R*=H) or ketones (R*=alkyl) of the formula (IV'), or to a salt thereof

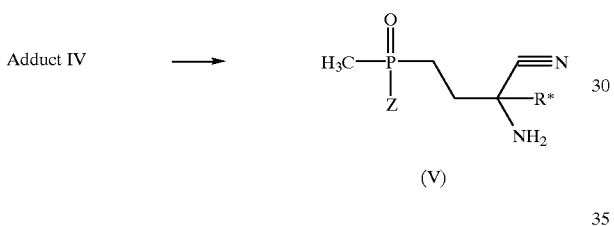

(IV')

in which Z is OH, $R^1$ or $R^2$, reacted under the conditions of a Strecker synthesis with ammonia/ammonium chloride and sodium cyanide or alternatively with mixtures of ammonia and hydrocyanic acid or with ammonia and a salt of hydrocyanic acid, if appropriate in the presence of ammonium chloride, to give the a-aminonitriles of the formula (V) or a salt thereof, Step 2:

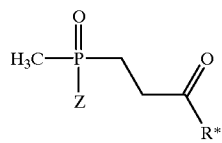 ⟶

(V)

where in the formulae (IV') and (V) the radical R* is as defined in formula (I) and Z is as defined in formula (IV') or is OH, and c) (Step 3)

the compound of the formula (V) is hydrolyzed under acidic or basic conditions to give the compound of the formula (I) or salts thereof.

17. The process according to claim 16, wherein $R^1$ and $R^2$ independently of one another are ($C_1$–$C_6$)alkoxy, ($C_1$–$C_6$)haloalkoxy, benzyloxy or phenoxy, where each of the two last-mentioned radicals is unsubstituted or substituted by one or more radicals selected from the group consisting of halogen, alkyl, haloalkyl, alkylthio, nitro, cyano, alkylsulfonyl and haloalkysulfonyl having in each case 1 to 6 carbon atoms in the alkyl moiety, or one of the radicals $R^1$ or $R^2$ is hydroxyl.

18. A process for preparing compounds of the formula I

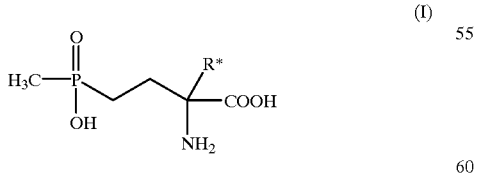

(I)

in which

R* is hydrogen or ($C_1$–$C_4$)-alkyl, or salts thereof with acids or bases, which comprises a) (Step 1)

reacting a trivalent methylphosphorus compound of the formula (II) with an unsaturated derivative of the formula (III), in the presence of a condensing agent or activator selected from substances which promote or catalyze the addition of the phosphorous component to the α, β-unsaturated keto compound and, if appropriate, alcohols, to give an adduct (IV), Step 1:

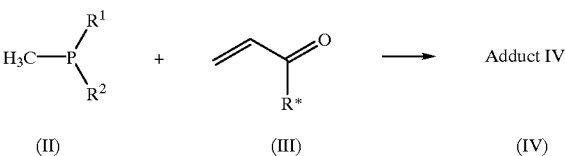

(II)   (III)   (IV)

wherein the formulae $R^1$ and $R^2$ independently of one another are ($C_1$–$C_{18}$) alkoxy with or without substitution, benzyloxy or phenoxy, which may also be substituted, or one of the radicals $R^1$ and $R^2$ is hydroxyl, and R* is as defined in formula (1), b) (Step 2)

the adduct (IV) is, if appropriate after hydrolysis to aldehydes (R*=H) or ketones (R*=alkyl) of the formula (IV), or to a salt thereof

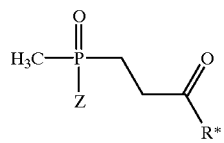

(IV')

in which Z is OH, $R^1$ or $R^2$, reacted under the conditions of a Strecker synthesis with ammonia/ammonium chloride and sodium cyanide or alternatively with mixtures of ammonia and hydrocyanic acid or with ammonia and a salt of hydrocyanic acid, if appropriate in the presence of ammonium chloride, to give the a-aminonitriles of the formula (V) or a salt thereof, Step 2:

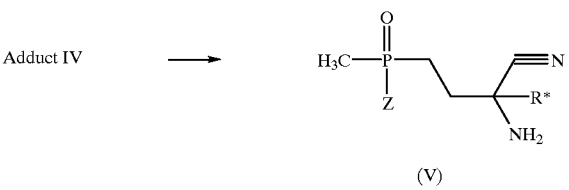

(V)

where in the formulae (IV') and (V) the radical R* is as defined in formula (I) and Z is as defined in formula (IV') or is OH, and c) (Step 3)

the compound of the formula (V) is hydrolyzed under acidic or basic conditions to give the compound of the formula (I) or salts thereof, wherein in step 1, as compounds (II), compounds of the formula (II-1) are reacted with a compound of the formula (III) in the presence of anhydrides $A_2O$ and alcohols ROH to give adducts (IV) of the formula (IV-1),

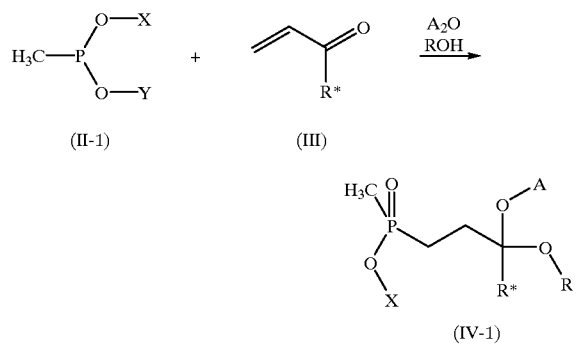

in which each of the radicals X and Y independently of one another is H or $(C_1-C_{18})$alkyl which is unsubstituted or substituted, benzyl or phenyl, where each of the two abovementioned radicals is unsubstituted or substituted, and A is an acyl radical, R is $(C_1-C_{18})$alkyl, which is unsubstituted or substituted, benzyl or phenyl, where each of the two radicals above is unsubstituted or substituted.

19. The process according to claim 18, wherein X, Y and R are each $(C_1-C_4)$alkyl, A is an acyl radical of an alkanecarboxylic acid having 1 to 6 carbon atoms and R* is a hydrogen atom.

* * * * *